United States Patent [19]

Kasten

[11] Patent Number: 5,145,367
[45] Date of Patent: Sep. 8, 1992

[54] VACUUM INSTRUMENT FOR DENTAL HYGIENE AND DENTAL TREATMENT

[75] Inventor: Werner Kasten, Belt-Schutsloot, Netherlands

[73] Assignee: Durr Dental GmbH & Co KG, Fed. Rep. of Germany

[21] Appl. No.: 460,912

[22] PCT Filed: Aug. 1, 1988

[86] PCT No.: PCT/EP88/00692
§ 371 Date: Feb. 12, 1990
§ 102(e) Date: Feb. 12, 1990

[87] PCT Pub. No.: WO89/01319
PCT Pub. Date: Feb. 23, 1989

[30] Foreign Application Priority Data

Aug. 12, 1987 [DE] Fed. Rep. of Germany ....... 3738811

[51] Int. Cl.$^5$ .................. A61C 1/10; A61C 1/12; A61C 17/02; A61C 17/06; A61C 17/14
[52] U.S. Cl. .................. 433/84; 433/80; 433/91; 433/95; 433/216
[58] Field of Search .................. 433/80, 81, 89, 91, 433/94, 95, 216

[56] References Cited

U.S. PATENT DOCUMENTS

| | | | |
|---|---|---|---|
| 3,164,153 | 1/1965 | Zorzi | 433/91 |
| 3,807,048 | 4/1974 | Malmin | 433/80 |
| 4,021,921 | 5/1977 | Detaille | 433/80 |
| 4,215,476 | 8/1980 | Armstrong | 433/80 |
| 4,248,589 | 2/1981 | Lewis | 433/80 |
| 4,340,365 | 7/1982 | Pisanu | 433/80 |
| 4,917,603 | 4/1990 | Haack | 433/29 |

*Primary Examiner*—Paul J. Hirsch
*Assistant Examiner*—C. A. Cherichetti
*Attorney, Agent, or Firm*—Fred Philpitt

[57] ABSTRACT

A vacuum instrument for dental hygiene and dental treatment which is intended to permit parodontological treatment of the tooth pockets. The instrument has an elastic suction cap which can produce a sealed vacuum over the gum pockets and interdental crevices. A treatment liquid is supplied to the suction cap and removed by the suction. Intermittent application of the vacuum produces a pumping action, which through likewise intermittent rinsing results in optimal cleaning of the interdental crevices as far as the base of the pocket.

13 Claims, 1 Drawing Sheet

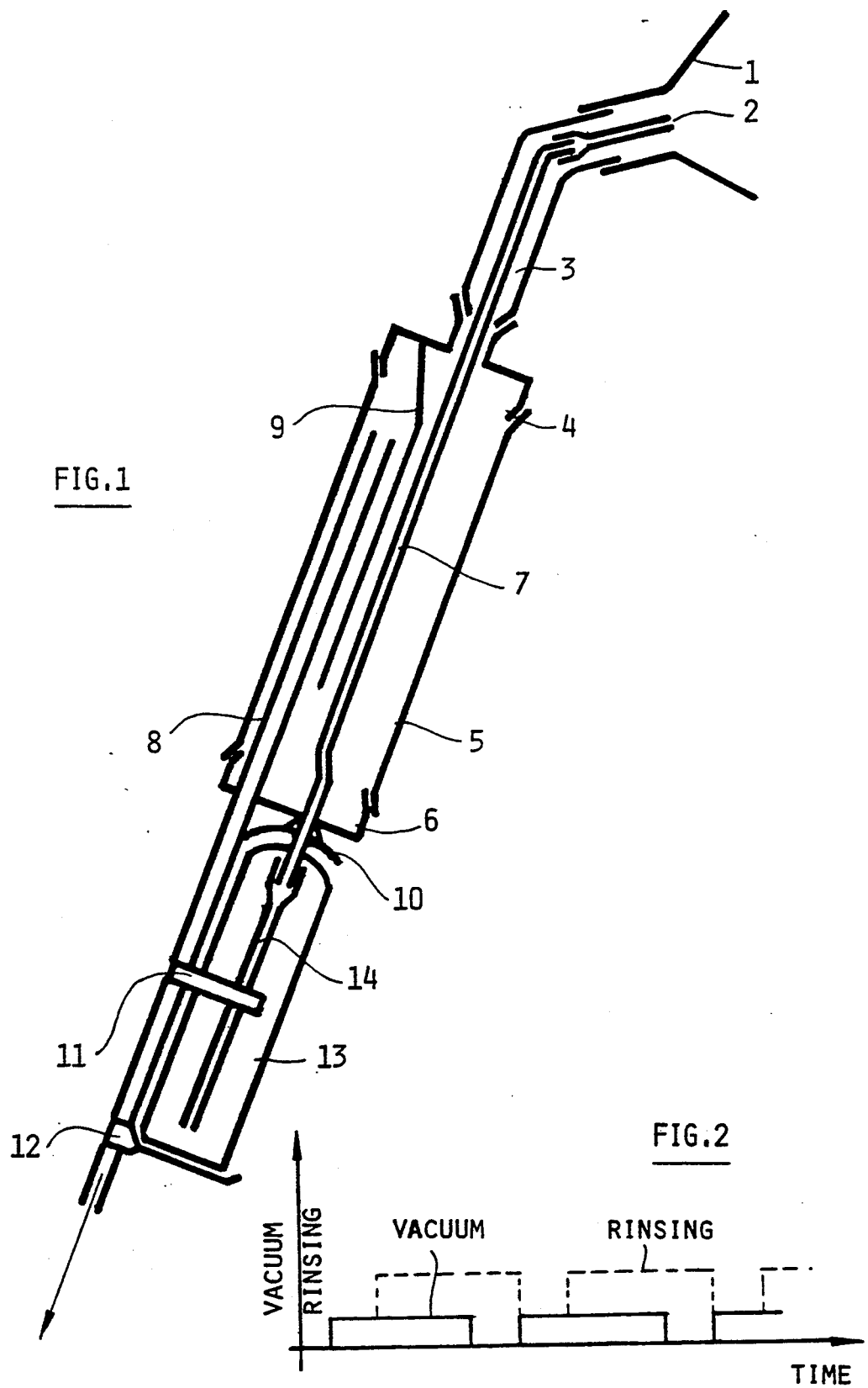

VACUUM INSTRUMENT FOR DENTAL HYGIENE AND DENTAL TREATMENT

The invention relates to a vacuum instrument for dental treatment, T.

A vacuum instrument for the treatment of the root canals of teeth is known from CH A 294 164. It serves for the treatment of tooth cavities for the purpose of rinsing and drying thereof. In this case, a suction cap with a conical wall is used in such a way that by appropriate expansion, as a cap, it encloses the crown of the tooth to be treated. In this state, by means of the reversible valve, instead of the vacuum pump, the supply of treatment solution is connected to the vacuum space produced, which then flows into the tooth as the vacuum disappears and can be removed again by subsequent evacuation. For the removal of the entire device, the valve is completely closed, whereupon the cap can be removed from the tooth.

For disinfectant treatment of the tooth, according to FR A 2 588 469, a U shaped body consisting of porous material, approximately adapted to the shape of a tooth, at the end of a toothbrush-like handle is known, which can be supplied from the grip of the handle with a treatment agent in such a way that on its inside it transfers this agent to the teeth. The treatment agent is placed under slight excess pressure for acting on the teeth.

In comparison therewith, the present invention provides a vacuum instrument, which is intended to permit parodontological treatment of the tooth pockets. Normally the crevice between the tooth pocket wall and tooth wall is not accessible for treatment, because this gap is closed by the capillary adhesion and is unreachable. These forces are greater the narrower the crevice. In this case, the gum with the interdental papillae lies directly on the surface of the tooth and in the region of the neck of the tooth and of the interdental gaps forms a very slender crevice, the so-called gum pockets, which may be of greater or lesser depth and which are under the action of the capillary forces. Despite the capillary adhesion, foreign bodies enter these free spaces, which can no longer be removed, so that in the bottom of the gum pocket, they are frequently subject to bacterial decomposition.

Due to the patent claims proposed in order to achieve the object set, the aforementioned capillary adhesion forces are overcome and the open crevices are made accessible to medication in a particularly effective manner.

BRIEF DESCRIPTION OF THE DRAWINGS

FIG. 1 is a side elevation of the vacuum instrument.
FIG. 2 is a graph of the vacuum and rinsing sequence.

The present invention is based on the fact that by means of the suction cap, a sealed vacuum can be produced over the gum pockets and interdental crevices. This is the prerequisite for the beginning of the action. As regards the type of action of the vacuum instrument, it should be mentioned in advance that in very narrow crevices, in which the lateral surfaces lie directly one against the other, molecular forces and attraction forces between wall and liquid molecules exist, which cause the phenomenon of "capillary adhesion", known by the term capillary tube effect. This manifests itself in that in a very narrow tube=capillary tube immersed in water, the water rises, so that the liquid level within the capillary tube is higher than outside. This sucking-in of the liquid is caused by the capillary attraction forces, which also draw liquids into crevices and retain them there intensively. The narrower the crevice, the greater the capillary action, thus it is inversely proportional to the narrowness of the cavity. These capillary forces are cancelled out by vacuum and the contents of the crevice are sucked outwards, i.e. into the vacuum. Solely under these conditions do the crevices set free and empty themselves of the contents (liquid and suspended particles located therein) previously retained by the capillary forces.

Similar conditions exist in the dental region. In this case, the gum with the interdental papillae rests directly on the surface of the tooth and in the region of the neck of the tooth and the interdental gaps forms an extremely slender crevice, the so-called gum pockets, which may have a greater or lesser depth and in which the capillary forces are likewise active. Due to the capillary adhesion forces, particles of food produced by chewing together with liquid inevitably pass into these crevices, which then no longer release the latter. Consequently, the food particles generally remain at the bottom of the gum pockets and at this point are frequently subject to fermentation and bacterial decomposition. The single possibility of reaching, i.e. opening up the depth of these capillary crevices is achieved, as mentioned above, by overcoming the capillary adhesion forces with the aid of a vacuum. Toothbrushes and oral rinsing are of no use here, in the absence of a vacuum.

One particular effect of the vacuum instrument is achieved by using an intermittent vacuum. When the vacuum is shut off, the capillary forces in the crevices again come into effect and draw in the rinsing liquid. On the other hand, due to renewed neutralisation of the capillary forces, renewed switching-on of the vacuum empties the crevice. The reverse effect is thus achieved, i.e. a pumping action is set up, which not only guarantees the actual rinsing-out of the gum pockets, but also facilitates the introduction of drugs to the very base of the pockets. Due to the inclusion of the intermittent vacuum, i.e. of the pumping action, a repeated exchange of the contents of the tooth pockets and thus maximum emptying of the crevice with regard to impurities (fermentable foreign substances, conglomerations of bacteria inter alia) is achieved. The principle is simple, the effect optimum, especially due to the fact that parodontic processes can not solely be prevented but the cause of them can be tackled.

With previously existing dental rinsing apparatus (German Patent Specifications Nos. 125 410, 181 904, 517 203, 572 741 and 729 861) the effect of removing the contents from gum pockets is not achieved, since in the latter the sealed vacuum over interdental crevices is missing. With these methods, as a result of the presistence of the capillary forces, the rinsing liquid cannot even penetrate the gum pockets, since the latter are not emptied. The purpose of rinsing is thus completely missed. The rinsing liquid sqirted on remains outside the crevices and is sucked off again solely from the surface of the gum by the suction cannula, without having fulfilled the function of deep cleaning.

According to the invention, the vacuum instrument achieves the object intended for it by the solution features described in the characterising part of Patent Claim 1.

The mounting apparatus for the rinsing liquid or drug ampoule on the handpiece also proved appropriate. The contents of the ampoules passes by way of a valvetype connection to the liquid tube and the cannula in the working region of the suction cap. The route by way of a liquid tube from the treatment unit would be too long and would make relatively simple monitoring of the admission of liquid impossible, quite apart from the lack of economy, since above all, when introducing drugs, a part thereof is left behind and would be lost.

The vacuum instrument for dental treatment acquires a particular aspect if one considers the opening-up of gum pockets from the point of view of effective cleaning thereof as regards foreign substances causing inflammation, since these very crevices are frequently to be regarded as the starting point of inflammation and feared dental caries. Considerable savings could be made on artificial dentures if such an instrument could be made commercially available.

The functional parts of the vacuum instrument for dental treatment are shown in the drawing. The replaceable funnel-shaped elastic suction cap 1 is seated on the suction pipe 3. The likewise replaceable rinsing cannula 2 is located within the suction cap. The two covers 4 and 6 can be attached to the handpiece 5, the suction tube 8 as well as the rinsing liquid tube 7 being attached to the cover 6. Located at the lower end of the rinsing liquid tube are the mounting parts 10, 11 and 12 for the rinsing liquid or drug ampoules 13. Located in the upper mounting 10 is an air-supply valve, in order that the rinsing liquid or the drug may pass due to the suction force of the existing vacuum into the liquid tube and the cannula in the working region of the suction cap. The lower mounting 12 is able to slide according to the size of the ampoule to be inserted. The liquid tube immersed in the ampoule is exchangeable (14) in the form of a cannula according to the size of the ampoule and the quantity of liquid (rinsing liquid or drug) to be introduced. Located in the region of the vacuum pump (not shown) is a shut-off as well as a rotary restriction valve, which regulates the vacuum value at between 100–150 mm Hg and on the other hand permits the intermittent vacuum for a sliding time interval of 1–5 seconds. The operation takes place by way of the handpiece.

The intermittent vacuum has particular functions on account of the pumping action caused thereby, in the region of the gum pockets. The addition of rinsing liquid takes place by introducing the rinsing liquid ampoule in the vacuum phase, since then the contents of the pockets are located outside, i.e. in the region of the pocket opening as a result of cancellation of the capillary forces, so that the rinsing liquid is mixed with the contents of the pocket and can be sucked out and removed according to the overflow principle = creation of head of liquid contact. This process can be made more intensive by adding the intermittent vacuum. If an interruption of the vacuum and ventilation of the suction funnel region occurs, possibly due to a rotary valve, then due to cancellation of the vacuum across the interdental cavity, the capillary forces again become effective and suck the rinsing liquid into the parodontal pockets. If this process is repeated a few times, i.e. the vacuum is utilised by switching-on for certain time intervals, finally solely rinsing liquid is present, which fills the entire pocket space to the very bottom, according to a methylene blue test. As an average time relationship, which can be adapted to the local situation, a time period of three seconds has proved successful for the alternating phases, a preliminary vacuum of one second occurring first, which is then followed by a rinsing phase of three seconds duration and thus the entire vacuum phase outlasts by one second. Due to the preliminary vacuum, first of all the crevice is emptied in an optimum manner. Due to the rinsing which then occurs, the contents of the pocket located at the upper edge of the pocket are rinsed away. After two seconds of this joint operation, the vacuum is again shut off, due to which, as a result of re-occurrence of the capillary forces, the rinsing liquid is sucked into the pocket. This operation is limited to one second. Then the vacuum (preliminary) is again initiated and with the beginning of rinsing the same operation is repeated, a sequence, which is referred to as intermittent vacuum (see FIG. 2, vacuum equals and rinsing equals). When adding drugs, the vacuum or respectively the liquid feed is operated separately, in order that the drug can drip onto the pocket opening. After shutting off the vacuum, the capillary forces become active for sucking-in the drug. Then, according to a methylene blue test, the drug has penetrated as far as the bottom of the pocket. Since, in the case of a brief liquid feed, only a few drops of the drug pass into the region of the pocket opening, this small quantity of liquid remains in the region of the edge of the gum—the overflow principle of rinsing does not come into play here—and when the vacuum is shut off is then sucked directly into the subgingival space. Relatively exact dosing is thus possible.

I claim:

1. An apparatus for vacuum dental treatment comprising
   (a) a cap-shaped suction member (1) having elastic edges which are adapted to be applied to the teeth and gum area, the geometry and the material of said suction member (1) being such that said elastic suction member overlies the juncture of the gums and teeth to form a closed treatment chamber, said treatment chamber including the gum pocket defined between a tooth and the adjacent gum,
   (b) a feed line (7) for intermittently supplying a plurality of increments of treatment liquid into said treatment chamber, the outer end of said cap-shaped suction member (1) extending beyond the outlet end of said feed line (7),
   (c) a vacuum source connected to said suction member (1),
   (d) means for adjusting the suction force exerted on the contents of said gum pocket by adjusting the vacuum within the suction member (1) to a value which exceeds the capillary adhesion force that exists in the gum pocket, and
   (e) control means for the vacuum source and the liquid feed line (7) for setting up a pumping action in the gum pocket which both effects sucking liquid out of the gum pocket and the introduction of treatment liquid to the base of the gum pocket, said control means being constructed to
      (a) establish a first treatment phase which causes the suction member (1) to operate under vacuum alone,
      (b) establish a sequential second treatment phase which causes the suction member (1) to operate under vacuum at the same time that a treatment liquid is supplied via said feed line (7) and
      (c) consecutively repeat the above sequence of first and second treatment phases a plurality of times whereby a repetitive pumping of treatment liquid both into and out of the gum pocket is achieved.

2. The apparatus as in claim 1, which includes means for controlling the suction member (1) so that it receives rinsing liquid via the feed line means (7).

3. The apparatus as in claim 1 which includes means for keeping the vacuum constant during the first and second phases of the treatment cycle.

4. The apparatus as in claim 1, said cap-shaped suction member (1) being dome-shaped or funnel-shaped.

5. The apparatus as in claim 1 wherein said cap-shaped suction member (1) is formed with a rim portion which is conical.

6. The apparatus as in claim 1 wherein the said feed line means (7) carries a discharge cannula (2) having a discharge end which projects into a space defined by the cap-shaped suction member (1).

7. The apparatus as in claim 6 wherein the discharge cannula (2) is removably connected to said feed line means (7).

8. The apparatus as in claim 1 wherein the said cap-shaped suction member (1) is removably connected to a working end of a suction line (3-6, 8) and the other end of said suction line is connected to said vacuum source.

9. The apparatus as in claim 8 wherein a section of said suction line (3-6, 8) is formed as a hand piece (5).

10. The apparatus as in claim 9 wherein the portion of said suction line means formed as a hand piece (5) is provided with mounting means (10-12) for receiving an ampoule (13), said ampoule (13) containing a treatment liquid and being connectable to the feed line means (7) by valve means.

11. The apparatus as claim 1 which includes means to set the vacuum prevailing in the cap-shaped suction member (1) to a value between 100 and 150 mm Hg.

12. The apparatus as in claim 1 which includes means to place said cap-shaped suction member (1) intermittently under vacuum, the vacuum application interval being continuously adjustable from 1 to 5 seconds.

13. The apparatus of claim 1 wherein said control means in a third phase of the treatment cycle causes liquid to be supplied via the feed line (7) while the suction member (1) is completely shut off from the vacuum source.

* * * * *